United States Patent [19]
Metivier

[11] Patent Number: 5,654,338
[45] Date of Patent: Aug. 5, 1997

[54] PREPARATION OF OPTICALLY ACTIVE α-(HYDROXYPHENOXY) ALKANECARBOXYLIC ACIDS AND DERIVATIVES THEREOF

[75] Inventor: Pascal Metivier, Ste Foy Les Lyon, France

[73] Assignee: Rhone-Poulenc Chimie, Courbevoie Cedex, France

[21] Appl. No.: 428,710

[22] Filed: Apr. 25, 1995

[30] Foreign Application Priority Data

Apr. 25, 1994 [FR] France ................... 94 04933

[51] Int. Cl.$^6$ ................................. C07C 69/76
[52] U.S. Cl. ................ 514/570; 560/75; 560/61; 562/401; 562/471
[58] Field of Search ............ 560/75, 61; 514/570; 562/401, 471

[56] References Cited

U.S. PATENT DOCUMENTS

| | | | |
|---|---|---|---|
| 4,625,053 | 11/1986 | Fujinawa et al. | 562/401 |
| 4,665,212 | 5/1987 | Makino et al. | 560/61 |
| 4,766,220 | 8/1988 | Gras | 546/302 |

FOREIGN PATENT DOCUMENTS

| | | |
|---|---|---|
| 0009285 | 4/1980 | European Pat. Off. . |
| 0082413 | 6/1983 | European Pat. Off. . |
| 0192849 | 9/1986 | European Pat. Off. . |
| 2460286 | 1/1981 | France . |
| 2486071 | 1/1982 | France . |
| 2854542 | 6/1980 | Germany . |

*Primary Examiner*—Margaret Glass
*Attorney, Agent, or Firm*—Burns, Doane, Swecker & Mathis, L.L.P.

[57] ABSTRACT

Optically active α-(hydroxyphenoxy)-alkanecarboxylic acids or derivatives thereof, for example D-2-(4-hydroxyphenoxy)propionic acid or lower alkyl ester thereof, are prepared by (a) saponifying an alkyl ester of an optically active α-halogeno-alkanecarboxylic acid, in an alcoholic solvent medium, by reacting same with an aqueous solution of an alkali metal hydroxide, thereby providing a solution of an alkali metal salt of an optically active α-halogeno-alkanecarboxylic acid, (b) next reacting the step (a) solution thus provided with a dihydroxybenzene or salt thereof, in the presence of an alkali metal hydroxide and in an alcoholic solvent medium, and thence (c) recovering the optically active α-(hydroxyphenoxy)-alkanecarboxylic acid or derivative thereof from the medium of reaction.

22 Claims, No Drawings

PREPARATION OF OPTICALLY ACTIVE α-(HYDROXYPHENOXY) ALKANECARBOXYLIC ACIDS AND DERIVATIVES THEREOF

BACKGROUND OF THE INVENTION

1. Technical Field of the Invention

The present invention relates to a novel process for the preparation of optically active α-(hydroxyphenoxy) alkanecarboxylic acids, and, more especially, to the preparation of optically pure D-2-(4-hydroxyphenoxy)propionic acid (hereinafter also abbreviated to "D-HPPA" for purposes of simplicity).

This invention also relates to the preparation of optically active derivatives of the α-(hydroxyphenoxy) alkanecarboxylic acids, in particular to the optically active alkyl esters thereof.

2. Description of the Prior Art

Aliphatic esters of optically pure D-2-(4-hydroxyphenoxy)propionic acid are intermediates for selective herbicides which currently are in great demand.

These esters can be obtained directly via a Walden inversion from an alkyl L-chloro- or L-bromopropionate and hydroquinone, in the presence of a strong base, in an aqueous or alcoholic reaction medium. Unfortunately, in these media the esters are readily hydrolyzed and the chloropropionic moiety is racemized, as described by W. A. Cowdrey et al, *Journal of the Chemical Society*, 1208 (1937).

These esters can also be prepared from D-2-(4-hydroxyphenoxy)propionic acid. However, there are two principal differences in the preparation of D-2-(4-hydroxyphenoxy)propionic acid: (1) manufacturing a product with high optical purity and, (2) obtaining a monosubstituted hydroquinone compound with high selectivity.

D-HPPA is synthesized utilizing the processes described in the prior art, in an alcoholic or aqueous medium.

Thus, JP-A-62/16,446 describes the preparation of D-HPPA by reacting a sodium salt of L-α-chloropropionic acid, in ethanolic solution, with hydroquinone in the presence of caustic acid. The process described is carried out in an anhydrous medium. The sodium salt of the L-α-chloropropionic acid is obtained from the methyl ester of L-α-chloropropionic acid added to an aqueous solution of sodium hydroxide, followed by elimination of the water by reduced pressure distillation to provide a white solid which is recovered and dissolved in ethanol.

This process must be carried out in an anhydrous medium which is very restricting from an industrial viewpoint and handling the solid is not easy, as the substance is quite sticky.

D-HPPA can be prepared in an aqueous medium; the two references indicated above illustrate this preparative technique.

EP-B-0,108,374 describes a process for the preparation of hydroxyphenoxy-alkanecarboxylic acids, including 2-(4-hydroxyphenoxy)propionic acid.

The distinguishing characteristic of the '374 process is to mix dihydroxybenzene in an alkaline solution with a 2-halogeno-alkanecarboxylic acid (or halide or ester thereof) at a temperature of less than 60° C., and then to continuously transfer the mixture through a tube reactor at temperatures of 80° C. to 120° C.

Monoalkylation is said to be obtained by the continuous passage of the reaction medium through the tube reactor for a short period of time, at a high temperature. This type of process requires specialized apparatus.

EP-A-0,192,849 describes the preparation of a derivative of an optically active (4-hydroxy-2-phenoxy)propionic acid, entailing reacting an alkaline salt of an optically active α-halogeno-propionic acid with dihydroxybenzene or an alkaline hydroquinone salt, in the presence of an alkali metal hydroxide and a suitable amount of water which will precipitate the disodium salt of the optically active (4-hydroxy-2-phenoxy)propionic acid. The water is employed in an amount such that the ratio of water/hydroquinone ranges from 1 to 2.5 by weight.

SUMMARY OF THE INVENTION

Accordingly, a major object of the present invention is the provision of an improved process for the preparation of an optically active α-(hydroxyphenoxy)alkanecarboxylic acid or derivative thereof, including D-HPPA, which avoids certain of the disadvantages and drawbacks of the prior art or which presents certain advantages thereover.

Briefly, the present invention features a process for the preparation of an optionally active α-(hydroxyphenoxy) alkanecarboxylic acid or derivative thereof, comprising:

(a) in a first step, preparing a solution of an alkaline salt of an optically active α-halogeno-alkanecarboxylic acid by saponification, in an alcoholic medium, of an alkyl ester of an optically active α-halogeno-alkanecarboxylic acid using an alkali metal hydroxide in aqueous solution, (b) in a second step, directly reacting the solution from the preceding step (a), comprising the alkaline salt of the a-halogeno-alkanecarboxylic acid with a dihydroxybenzene or an alkaline salt of a dihydroxybenzene, in the presence of an alkali metal hydroxide and in an alcoholic solvent, and (c) in a final step, recovering the optionally active α-(hydroxyphenoxy)alkanecarboxylic acid or derivative thereof from the medium of reaction.

DETAILED DESCRIPTION OF BEST MODE AND PREFERRED EMBODIMENTS OF THE INVENTION

More particularly according to the present invention, it has now unexpectedly been found that the production of an α-(hydroxyphenoxy)alkanecarboxylic acid from the alkyl ester of an α-halogeno-alkanecarboxylic acid could only be carried out, in an alcoholic medium and continuously, and without racemization, if the alkyl ester of the α-halogeno-alkanecarboxylic acid were saponified prior to contacting it with the dihydroxybenzene in the form of a salt thereof.

The process of the invention is carried out in an alcoholic medium which presents the advantage of a higher reaction rate and, thus, an increase in productivity.

It is of particular interest when preparing esters, since the esterification reaction can be carried out subsequently in the alcohol.

The process is carried out without racemization and the optical yield, i.e., the ratio expressed as a percentage between the enantiomeric excess of the α-(hydroxyphenoxy)alkanecarboxylic acid and the enantiomeric excess of the alkyl ester of the α-halogeno-alkanecarboxylic acid is close to 100%, and most typically ranges from 98% to 100%.

The process of the invention is most preferably suitable for the preparation of α-(hydroxyphenoxy)alkanecarboxylic acids having the following general formula (I):

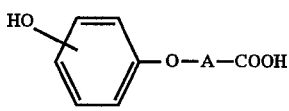

in which A is a methylene radical which may be substituted by 1 or 2 alkyl radicals having from 1 to 4 carbon atoms, preferably a methyl radical, and the hydroxy group is in the 2-, 3- or 4- position with respect to the ether function.

The acid obtained is an optically active compound, and the optically active carbon atom is the carbon atom which is α- to the COOH group.

In the first step of the process of the invention, a solution of an alkaline salt of an optically active α-halogeno-alkanecarboxylic acid is prepared by saponification, in alcoholic medium, of an alkyl ester of an optically active α-halogeno-alkanecarboxylic acid by means of an alkali metal hydroxide in aqueous solution.

An alkyl ester of an α-halogeno-alkanecarboxylic acid having the formula (II) is advantageously used:

in which A is a methylene radical which may be substituted by 1 or 2 alkyl radicals having from 1 to 4 carbon atoms, preferably a methyl radical, R is a linear or branched alkyl radical having from 1 to 4 carbon atoms, and X is a halogen atom, preferably a chlorine or bromine atom.

Particularly exemplary compounds of formula (II) include the methyl or ethyl esters of the following carboxylic acids in their D or L form:

α-Chloroacetic acid,
α-Bromoacetic acid,
α-Chloropropionic acid,
α-Bromopropionic acid,
α-Chlorobutyric acid,
α-Bromobutyric acid,
α-Chloroisobutyric acid,
α-Bromoisobutyric acid.

Among these esters, the L or D isomer of α-chloropropionic acid is the preferred.

The alkaline salt of the optically active α-halogeno-alkanecarboxylic acid is thus prepared from the alkyl ester by reacting the latter with an alkali metal hydroxide in aqueous solution in an alcoholic medium.

Preferably, the ester is selected such that the alcohol liberated on saponification is the same as the alcohol employed as the reaction solvent.

The optical isomer of formula (II) with the desired D or L configuration is used, taking account that the reaction inverts the stereochemistry of the starting isomer.

Preferably, the compound of formula (II) has a high degree of optical purity, generally less than 10% of the other enantiomer, preferably less than 5%, and more preferably less than 3%.

Compounds of formula (II) which satisfy the above criteria are commercially available, in particular the methyl ester of L-α-chloropropionic acid marketed by RHÔNE-POULENC.

The saponification agent is an alkaline agent, preferably sodium or potassium hydroxide.

Sodium hydroxide is the preferred.

The alkaline agent can be used in the form of an aqueous solution, or as a solid with parallel addition of the water required to dissolve it.

The concentration of the aqueous alkaline hydroxide solution advantageously ranges from 30% to 60% by weight. Commercially available solutions are suitable, in particular the 36% by weight sodium hydroxide solution.

The base is generally used in excess. The amount is such that the ratio between the number of moles of alkali metal hydroxide and the number of moles of alkyl ester of the α-halogeno-alkanecarboxylic acid preferably ranges from 1.0 to 1.2.

The saponification reaction is carried out in an alcoholic medium. The alcohol employed as the reaction solvent is characteristically a primary alcohol having from 1 to 4 carbon atoms.

Preferably, methanol or ethanol is used, more preferably methanol.

It is also preferable to employ an alcohol having a high degree of chemical purity, preferably greater than 90%.

The amount of alcohol used is determined such that it represents 5% to 40% of the weight of the salt of the α-halogeno-alkanecarboxylic acid.

The saponification reaction temperature preferably ranges from 0° C. to 40° C., more preferably from 20° C. to 25° C.

The reaction is advantageously carried out at atmospheric pressure.

In one embodiment of the present invention, the alkali metal hydroxide solution is introduced into the reaction medium comprising the alkyl ester of the α-halogeno-alkanecarboxylic acid and conversely. This addition is gradual, in fractions, either continuously or discontinuously.

The rate of addition is such that the temperature is maintained within the limits indicated above, as the saponification reaction is exothermic.

The reaction mixture is stirred continuously.

After saponification, the alcoholic solvent is introduced in the amount indicated above. It can also be introduced prior to saponification, with the alkyl ester.

According to the process of the present invention, in the second step the solution from the first step, containing the alkaline salt of the α-halogeno-alkanecarboxylic acid, is reacted with dihydroxybenzene, or an alkaline salt of dihydroxybenzene, in the presence of an alkali metal hydroxide and in an alcoholic solvent.

A dihydroxybenzene having the formula (III) is typically employed:

in which the hydroxy group is in the 2-, 3- or 4-position with respect to the hydroxy group.

The preferred dihydroxybenzene of formula (III) is hydroquinone.

To reiterate, it is preferable to use a dihydroxybenzene having a high degree of chemical purity, preferably greater than or equal to 98%.

The dihydroxybenzene is reacted in a salt form thereof which can be obtained by adding an alkaline agent at the same time as the alkaline salt of the α-halogeno-alkanecarboxylic acid.

Preferably, the dihydroxybenzene is first salified, in an alcoholic medium, by reacting it with an alkaline agent before contacting it with the alkaline salt of the α-halogeno-alkanecarboxylic acid.

The alkaline agent used is preferably the same as that employed in the saponification step, most preferably in the same form.

The base is generally employed in a stoichiometric excess. The amount is such that the ratio between the number of moles of alkali metal hydroxide and the number of moles of dihydroxybenzene preferably ranges from 2.0 to 2.2.

The salification reaction is carried out in an alcoholic medium. The alcohol used is preferably that employed in the preceding step.

The amount of alcohol is determined such that it constitutes 100% to 300% of the weight of the dihydroxybenzene used, preferably about 150%.

The salification reaction temperature is not critical. It preferably ranges from 20° C. to 60° C.

The reaction is advantageously carried out at atmospheric pressure.

The reaction is preferably carried out in an inert gas atmosphere which can be nitrogen or a noble gas, preferably argon.

As a practical matter, the alkali metal hydroxide in a solid or an aqueous solution is introduced into the reaction medium comprising the dihydroxybenzene and the alcoholic solvent. This addition is gradual, in fractions, either continuously or discontinuously.

The rate of addition is such that the temperature is maintained within the limits indicated above, as the salification reaction is exothermic.

The reaction medium is continuously stirred.

The dihydroxybenzene is then reacted in the form of its alkaline double salt with the solution from the preceding step, comprising the alkaline salt of the α-halogeno-alkanecarboxylic acid.

The amount of reactants employed is such that the ratio between the number of moles of salified dihydroxybenzene and the number of moles of alkaline salt of the α-halogeno-alkanecarboxylic acid advantageously ranges from 1.0 to 1.5.

The reaction temperature is preferably less than 60° C., more particularly ranging from 30° C. to 55° C. and more preferably from 40° C. to 45° C.

In a preferred embodiment of the invention, the solution from the preceding step is gradually introduced into the reaction medium comprising the dihydroxybenzene in the form of its salt.

The reaction is completed by stirring the reaction mixture for a period of time preferably ranging from 1 to 3 hours. This operation is not critical, however.

In the final step, optically active α-(hydroxyphenoxy) alkanecarboxylic acid is recovered via known technique.

At the end of the reaction, a strong acid such as, for example, hydrochloric acid, sulfuric acid or phosphoric acid, generally as an aqueous solution thereof, is added to neutralize the reaction medium to a pH of about 7.0. The acid solution concentration is not critical. Hydrochloric acid is preferred. The concentration of the hydrochloric acid preferably corresponds to the concentration of the commercially available form, i.e., 37% by weight.

The single salt of the α-(hydroxyphenoxy)-alkanecarboxylic acid is thus obtained.

The alcoholic solution and the alcohol formed are eliminated by distillation.

The hydroquinone (or the compound of formula (III)) is extracted from the reaction medium using an organic solvent, preferably a ketone, more preferably methylisobutyl ketone, or an ether type solvent such as, for example, methyl-tert-butylether or ethyl-tert-butylether.

After separating the organic and aqueous phases, the residual aqueous solution is distilled to eliminate the organic solvent in solution in the aqueous phase. It is then acidified to a pH less than or equal to 1 to precipitate the α-(hydroxyphenoxy)-alkanecarboxylic acid.

In another embodiment of the invention, alkyl esters (which preferably have from 1 to 4 carbon atoms) are prepared, of optically active α-(hydroxyphenoxy)-alkanecarboxylic acids from α-(hydroxyphenoxy)-alkanecarboxylic acids obtained via the process described above, using any method known to this art.

These esters can be prepared very easily according to the process of the invention. The aqueous phase is neutralized to a pH less than or equal to 2.0 by addition of a strong acid as described above, preferably hydrochloric acid, followed by heating under reflux with an alkanol (preferably methanol) to obtain the ester corresponding to the alkanol (preferably the methyl ester).

The ester obtained is recovered from the reaction medium by any known means, for example distillation or crystallization.

The process of the invention is particularly well suited for the preparation of D-2-(4-hydroxyphenoxy)propionic acid.

In order to further illustrate the present invention and the advantages thereof, the following specific examples are given, it being understood that same are intended only as illustrative and in nowise limitative.

The following abbreviations, transformation ratio (TR), yield (YY) and selectivity (SE), have the following definitions:

$$TR_{HQ} = \frac{\text{number of moles of hydroquinone transformed}}{\text{number of moles of hydroquinone introduced}}, \%$$

$$YY_{HPPA/HQ} = \frac{\text{number of moles of (4-hydroxyphenoxy)propionic acid formed}}{\text{number of moles of hydroquinone introduced}}, \%$$

$$SE_{HPPA/HQ} = \frac{\text{number of moles of (4-hydroxyphenoxy)propionic acid formed}}{\text{number of moles of hydroquinone transformed}}, \%$$

$$YY_{HPPA/L-CPM} = \frac{\text{number of moles of (4-hydroxyphenoxy)propionic acid formed}}{\text{number of moles of methyl ester of } \alpha\text{-chloropropionic acid introduced}}, \%$$

$$\text{Optical purity}_{L-CPM} = \frac{\text{L-CPM}}{\text{L-CPM} + \text{D-CPM}}$$

$$\text{Optical purity}_{D-HPPA} = \frac{\text{D-HPPA}}{\text{D-HPPA} + \text{L-HPPA}}$$

EXAMPLE 1

(a) Preparation of sodium salt of L-α-chloropropionic acid:

90.1 g of the methyl ester of L-α-chloropropionic acid (L-CPM) with an optical purity of 97% were introduced into a three-necked flask provided with a dropping funnel and a mechanical stirrer.

90 g of an aqueous 36% by weight caustic soda solution were added over 30 minutes, maintaining the mixture at 25°–30° C. using a brine bath.

This mixture was permitted to stand for 1 hour at room temperature.

A white gel was obtained which was dissolved by adding 20 g of methanol.

(b) Preparation of D-2-(4-hydroxyphenoxy)-propionic acid:

180 g of methanol, followed by 88 g of 98% pure ground caustic soda, were placed in the bottom of a reactor provided with a double envelope, a temperature probe, a mechanical stirrer and a dropping funnel, with a coolant mounted above it and swept with a current of nitrogen. The temperature was maintained at 30° C.

121 g of hydroquinone were added in portions over 15 minutes, under nitrogen and at a stirring rate of 350 revolutions/minutes.

The mixture was heated to 45° C. and 205 g of the solution obtained from step (a) were added over 7 hours, 30 minutes.

This was maintained for two hours at 45° C., with stirring and under nitrogen.

It was then neutralized to a pH of 7 using 157.5 g of an aqueous 37% hydrochloric acid solution.

The total mixture was dissolved in deionized water and analyzed using high performance liquid chromatography.

The results obtained were as follows:

$$TR_{HQ} = 58.2\%$$
$$YY_{HPPA/HQ} = 50.4\%$$
$$SE_{HPPA/HQ} = 86.6\%$$
$$YY_{HPPA/L-CPM} = 75.3\%$$

$$\frac{\text{D-HPPA}}{\text{D-HPPA} + \text{L-HPPA}} = 96\%$$

In the following comparative example, D-2-(4-hydroxyphenoxy)propionic acid was prepared directly from L-CPM without carrying out prior saponification.

EXAMPLE 2 (Comparative)

Preparation of D-2-(4-hydroxyphenoxy)propionic acid 200 g of methanol and 52.3 g of water were placed in the bottom of a reactor as described in part (b) of Example 1, followed by 121 g of ground caustic soda in portions, maintaining the mixture at 30° C. with stirring at 350 revolutions/minute.

121 g of hydroquinone were added in portions over 15 minutes, under nitrogen and at 350 revolutions/minute.

The mixture was heated to 45° C. with stirring (350 revolutions/min.) and under nitrogen.

The mixture was cooled to 20° C., then neutralized to a pH of 7 using 160 g of an aqueous 37% hydrochloric acid solution.

This was dissolved in deionized water and analyzed using high performance liquid chromatography.

The results obtained were as follows:

$$TR_{HQ} = 51.4\%$$
$$YY_{HPPA/HQ} = 45.7\%$$
$$SE_{HPPA/HQ} = 89\%$$
$$YY_{HPPA/L-CPM} = 68.4\%$$

$$\frac{\text{D-HPPA}}{\text{D-HPPA} + \text{L-HPPA}} = 91\%$$

This comparative example shows the importance of carrying out prior saponification of the methyl ester of the L-α-chloropropionic acid in order to preserve a high optical yield.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an optically active α-(hydroxyphenoxy)alkanecarboxylic acid or derivative thereof without substantial racemization, comprising (a) saponifying an alkyl ester of an optically active α-halogeno-alkanecarboxylic acid, in an alcoholic solvent medium, by reacting said alkyl ester contained in said alcoholic sovlent medium with an aqueous solution of an alkali metal hydroxide, thereby providing a solution of an alkali metal salt of an optically active α-halogeno-alkanecarboxylic acid, (b) next reacting the step (a) solution thus provided with a dihydroxybenzene or salt thereof, in the presence of an alkali metal hydroxide and in an alcoholic solvent medium, and thence (c) recovering said optically active α-(hydroxyphenoxy)-alkanecarboxylic acid or derivative thereof from the medium of reaction.

2. The process as defined by claim 1, said alkyl ester of an α-halogeno-alkanecarboxylic acid having the formula (II):

in which A is a methylene radical or a methylene radical substituted by 1 or 2 alkyl radicals having from 1 to 4 carbon atoms, R is a linear or branched alkyl radical having from 1 to 4 carbon atoms, and X is a halogen atom.

3. The process as defined by claim 2, wherein formula (II), X is a chlorine or bromine atom.

4. The process as defined by claim 3, said alkyl ester of an optically active α-halogeno-alkanecarboxylic acid comprising an optically active methyl or ethyl ester of α-chloroacetic acid, α-bromoacetic acid, α-chloropropionic acid, α-bromopropionic acid, α-chlorobutyric acid, α-bromobutyric acid, α-chloroisobutyric acid or α-bromoisobutyric acid.

5. The process as defined by claim 1, said step (a) aqueous solution of an alkali metal hydroxide comprising a 30% to 60% by weight concentrated aqueous solution of sodium or potassium hydroxide.

6. The process as defined by claim 1, wherein step (a) the ratio between the number of moles of alkali metal hydroxide to the number of moles of alkyl ester of the α-halogeno-alkanecarboxylic acid ranges from 1.0 to 1.2.

7. The process as defined by claim 1, said alcoholic solvent medium comprising to the alcohol liberated during saponification.

8. The process as defined by claim 7, said alcoholic solvent medium comprising methanol or ethanol.

9. The process as defined by claim 1, wherein step (a) the amount of alcohol comprises from 5% to 40% of the weight of the salt thus produced.

10. The process as defined by claim 1, said step (a) being carried out at a temperature ranging from 0° to 40° C.

11. The process as defined by claim 1, said step (a) comprising introducing the solution of the alkali metal hydroxide into the medium of saponification which comprises the alkyl ester of the α-halogeno-alkanecarboxylic acid and adding said alcoholic solvent thereto either at the beginning or end of step (a).

12. The process as defined by claim 1, said dihydroxybenzene having the formula (III):

in which the hydroxy substituent is in the 2-, 3- or 4-position relative to the fixed hydroxy group.

13. The process as defined by claim 12, said dihydroxybenzene compound (III) comprising hydroquinone.

14. The process as defined by claim 1, said step (b) comprising reacting the step (a) solution with an alkali metal salt of said dihydroxybenzene.

15. The process as defined by claim 1, wherein step (b) the amount of alcohol comprises from 100% to 300% of the weight of said dihydroxybenzene.

16. The process as defined by claim 1, said step (b) comprising introducing the alkali metal hydroxide into a reaction medium which comprises said dihydroxybenzene and said alcoholic solvent.

17. The process as defined by claim 14, wherein the ratio between the number of moles of dihydroxybenzene salt and the number of moles of alkali metal salt of the optically active α-halogeno-alkanecarboxylic acid ranges from 1.0 to 1.5.

18. The process as defined by claim 14, comprising gradually introducing said step (a) solution into the step (b) medium of reaction wherein the step (b) medium of reaction comprises a dihydroxybenzene or a salt thereof, and an alkali metal hydroxide contained in an alcoholic solvent medium.

19. The process as defined by claim 1, said step (c) comprising precipitating α-(hydroxyphenoxy)-alkanecarboxylic acid.

20. The process as defined by claim 1 for the preparation of an alkyl ester of an optically active α-(hydroxyphenoxy) alkanecarboxylic acid, further comprising neutralizing the step (c) medium of reaction, heating same to the alcohol reflux to obtain the corresponding ester thereof, and recovering said ester.

21. The process as defined by claim 1, comprising the preparation of D-2-(4-hydroxyphenoxy)propionic acid or lower alkyl ester thereof.

22. The process of claim 1, wherein said reaction process is affected entirely at a temperature of less than 60° C.

* * * * *